(12) United States Patent
Taylor (10) Patent No.: US 6,544,291 B2
(45) Date of Patent: Apr. 8, 2003

(54) SUTURELESS GASTROESOPHAGEAL ANTI-REFLUX VALVE PROSTHESIS AND TOOL FOR PERORAL IMPLANTATION THEREOF

(76) Inventor: Thomas V. Taylor, 1806 Vassar, Houston, TX (US) 77098

( * ) Notice: Subject to any disclaimer, the term of this patent is extended or adjusted under 35 U.S.C. 154(b) by 0 days.

(21) Appl. No.: 09/681,364

(22) Filed: Mar. 26, 2001

(65) Prior Publication Data

US 2001/0020189 A1 Sep. 6, 2001

Related U.S. Application Data

(63) Continuation-in-part of application No. 08/987,693, filed on Dec. 9, 1997, now Pat. No. 6,254,642.

(51) Int. Cl.[7] .............................. A61F 2/04; A61F 2/06
(52) U.S. Cl. .................................... 623/23.68; 623/1.25
(58) Field of Search .......................... 623/23.68, 1.24, 623/2.26, 2.1, 1.26

(56) References Cited

U.S. PATENT DOCUMENTS

| | | | | |
|---|---|---|---|---|
| 4,056,854 A | * | 11/1977 | Boretos et al. ............... | 623/2.1 |
| 4,265,694 A | * | 5/1981 | Boretos et al. ............. | 156/242 |
| 4,957,508 A | * | 9/1990 | Kaneko et al. ............... | 623/12 |
| 5,163,953 A | * | 11/1992 | Vince ........................... | 623/2 |
| 5,314,473 A | * | 5/1994 | Godin ......................... | 623/12 |
| 5,411,552 A | * | 5/1995 | Andersen et al. ............... | 623/2 |
| 5,855,601 A | * | 1/1999 | Bessler et al. .................. | 623/2 |
| 5,861,036 A | * | 1/1999 | Godin ......................... | 623/12 |
| 6,287,334 B1 | * | 9/2001 | Moll et al. .................. | 623/1.24 |

FOREIGN PATENT DOCUMENTS

| | | |
|---|---|---|
| EP | 0857471 | 8/1998 |
| WO | 9629954 | 10/1996 |

OTHER PUBLICATIONS

Dua, Kulwinder S., MD et al, "Self Expanding Metal Esophageal Stent With Anti–Reflux Mechanism," *Gastrointestinal Endoscopy*, vol. 53, No. 6, p. 603 (2001).

Valbuena, Jose, MD, "Palliation of Gastroesophageal Carcinoma With Endoscopic Insertion of a New Antireflux Prosthesis," Gastrointestinal Endoscopy, vol. 30, No. 4, p. 241 (1984).

Nunes, Carlos C., et al, "Comparative Post–operative Study of Prostheses, with and without an Anti–Reflux Valve System, In the Palliative Treatment of Esophageal Carcinoma," Hepato–Gastroenterology, vol. 46, pp. 2859–2864 (1999).

* cited by examiner

Primary Examiner—Corrine McDermott
Assistant Examiner—Alvin Stewart
(74) Attorney, Agent, or Firm—Daniel N. Lundeen; Lundeen & Dickinson, LLP (57) ABSTRACT

Disclosed are an instrument, valve prosthesis and procedure for the minimally invasive implantation of a sutureless anti-reflux valve in a patient for the treatment of gastroesophageal reflux disease. A prosthesis is provided that comprises a cylindrical housing, a mounting ring and a one-way anti-reflux valve depending from the mounting ring. The cylindrical housing is constructed of a memory material that can be fixed in the gastroesophageal junction. The mounting ring and the anti-reflux valve are fixed within the housing.

25 Claims, 8 Drawing Sheets

SUTURELESS GASTROESOPHAGEAL ANTI-REFLUX VALVE PROSTHESIS AND TOOL FOR PERORAL IMPLANTATION THEREOF

CROSS REFERENCE TO RELATED APPLICATIONS

This is a continuation-in-part of my earlier copending application Ser. No. 08/987,693, filed Dec. 9, 1997, now U.S. Pat. No. 6,254,642.

BACKGROUND OF INVENTION

This invention relates to a device and non-invasive surgical method for treating gastroesophageal reflux disease. More specifically, it relates to an anti-reflux valve prosthesis and associated instrumentation for its peroral placement and in situ fixing at the gastroesophageal junction, to prevent the reflux of gastric contents into the esophagus in the treatment of gastroesophageal reflux disease in a patient.

Gastroesophageal reflux disease (GERD) is the commonest cause of dyspepsia, affecting some 30% of the United States adult population intermittently and some 10% on a continuous and troublesome basis. Gastroesophageal reflux disease produces heartburn, abdominal pain and regurgitation of acid-containing gastric contents into the esophagus and pharynx. It may also lead to alteration of the lining of the esophagus (Barrett's Esophagus), which may go on to produce esophageal cancer. Current methods of treating GERD include powerful antacid medication therapies and surgical interventions.

Medication therapy with powerful antacids is directed at treating the symptoms of GERD, and is necessarily not curative. Furthermore, medication-based therapies are not always fully effective, as reflux is not prevented and the esophagus may continue to be exposed to gastric content.

Surgical intervention typically involves either open surgery (performed through the abdomen or the chest) or laparoscopic surgery (performed through one or more incision access ports inserted through the abdominal wall), and the re-sectioning of tissue or the implanting of a prosthetic device. Although surgical interventions can be curative, these treatments are seriously invasive and have the attendant risk of such procedures. Despite the risk, the field has been motivated to provide solutions to the GERD problem, which has resulted in the development of a number of surgically implantable anti-reflux valve prosthetic devices. Prior anti-reflux valve prostheses are essentially one-way valves implanted at the gastroesophageal junction using open or laparoscopic surgery. The implanted prosthesis allows normal swallowing to take place in an orthograde manner while preventing the reflux of gastric contents from the stomach into the esophagus.

Examples of surgically implanted esophageal anti-reflux valve prostheses include the devices of: Godin (U.S. Pat. No. 5,314,473) which discloses a one-way, antivalve comprising a flattened tubular part associated with an annular fixing element; and Reich (U.S. Pat. No. 4,846,836) which discloses a bi-directional valve and housing for similar purposes. These devices were developed to be inserted into the gastro-esophageal junction via open or laparoscopic surgery and fixed there. The purpose was to permit the unidirectional passage of ingested materials into the stomach while preventing the reflux of gastric content of the stomach into the esophagus. Typically, these devices require suturing or other means to fix them to the tissue of the esophagus.

Generally, all of these prior devices and methods require surgical invasion of a body cavity and breach of the body membrane in some fashion (e.g., open surgery or laparoscopy) in order to accomplish their utility. However, such invasive surgical interventions are too frequently complicated by problems such as stricture formation, "gas bloat," or recurrent symptoms of reflux disease. Additionally, the results obtained by gross surgical treatment can be technique-dependent and vary significantly from surgeon to surgeon.

In view of the preference for minimally invasive forms of surgery there is a need in the art for GERD treatments that can be fully accomplished without surgically compromising the integrity of a patient's body membrane. Applicant has invented a peroral procedure for the insertion and implantation of a sutureless anti-reflux valve prosthesis that can address this need. It benefits the field to have an alternative prosthetic device and method that can be practiced to position and fix an anti-reflux prosthesis in place in the esophagus without resort to surgical incision or laparoscopy.

SUMMARY OF INVENTION

The present invention relates to an anti-reflux valve prosthesis system for treating gastroesophageal reflux disease (GERD) in a patient, which does not require open or laparoscopic surgery to implant. The present invention provides for perorally inserting a sutureless anti-reflux valve prosthesis down the lumen of the esophagus, to the gastroesophageal junction, where it is fixed in place. The advantage of this system is that peroral insertion of such a valve eliminates the need for either open formal laparotomy, thoracotomy or a laparoscopic approach using multiple access ports. Peroral installation of an anti-reflux prosthesis has the potential benefit of reducing the trauma, morbidity and hospital stay associated with implantation of anti-reflux valve prostheses relative to other surgical techniques. Furthermore, a system permitting the implantation of a standardized anti-reflux valve in an accurate and reproducible manner has the potential for providing more consistent clinical results than can be achieved with other techniquemethods of treatment.

A preferred embodiment of the present invention provides a prosthesis comprising a cylindrical housing, a mounting ring and a one-way anti-reflux valve. The cylindrical housing is constructed of a memory material that can be fixed in the distal esophagus. The mounting ring and the anti-reflux valve are fixed within the housing.

Similar cylindrical devices have been used (without the incorporation of an anti-reflux valve prosthesis) in the treatment of strictures due to esophageal cancer. An example of such a device is the WALLSTENT® esophageal endoprosthesis (Schneider USA, Inc.). These devices typically comprise a cylinder of memory metal in close contact with a sleeve of suitable material, such as silicone. The prosthesis is inserted perorally and positioned using an adaptation of the usual tool used for installing similar cylindrical devices. The prosthesis is fixed in place by the expansion of the cylindrical device housing the anti-reflux valve.

Another embodiment of the present invention provides an anti-reflux prosthesis comprising a cylindrical housing having an enlarged upper end, an optionally enlarged or bell-shaped lower end, and an interior defined by an interior wall. The cylindrical housing is constructed of a memory material having a normal cross-section. When a force, applied to the housing to make the cross-section small, is removed, the housing returns to its normal cross-section, or is expandable to its normal cross-section, e.g. by a balloon. A mounting ring is fixed to the interior wall of the upper end of the housing. Depending from the mounting ring within the interior of the cylindrical housing is a one-way valve. The present invention further comprises an optional anti-inversion support having two ends, one end of which is fixed to a lower end of the one-way valve and the other end of which is fixed to the wall of the lower end of the cylindrical housing.

Another aspect of the invention is the provision of a system for peroral insertion and mounting of the ant-reflux valve prosthesis in the gastroesophageal junction. The system includes an overtube for holding the cylindrical housing in a radially compressed condition at a distal end of the overtube for peroral insertion down an esophageal lumen. A stylet indwelling in the overtube is in releasable operative engagement with the housing to eject the housing from the distal end of the overtube. A balloon is preferably disposed at a distal end of the stylet within the cylindrical housing, wherein the balloon is in fluid communication with a central longitudinal passage in the stylet for introducing fluid into the balloon to facilitate expansion of the housing to its normal cross-section following ejection of the housing from the overtube, and for removing said fluid from the balloon to allow retraction of the balloon from the housing into the overtube.

In a further aspect, the invention provides a method for perorally implanting an anti-reflux valve prosthesis for treating gastroesophageal reflux disease before esophageal cancer. The method comprises: (a) perorally inserting the anti-reflux valve prosthesis described above in a radially compressed condition down the esophageal lumen: (b) positioning the compressed anti-reflux valve prosthesis near the esophageal junction; and (c) expanding the anti-reflux valve prosthesis to normal cross-section to implant said prosthesis in the esophageal junction. The insertion is preferably effected with the valve prosthesis in an overtube, the positioning preferably includes ejecting the valve prosthesis from the overtube, and the expanding optionally comprises inflating a balloon inside the valve prosthesis.

DETAILED DESCRIPTION

As exemplified by the figures, the present invention provides a peroral prosthesis system for treatment of gastroesophageal reflux disease (GERD) in a patient comprising an anti-reflux valve prosthesis, and a peroral implantation tool for perorally inserting and positioning the valve prosthesis at the distal end of the lumen of the esophagus, and implanting or fixing the valve prosthesis to the lumen wall.

Figure 1:
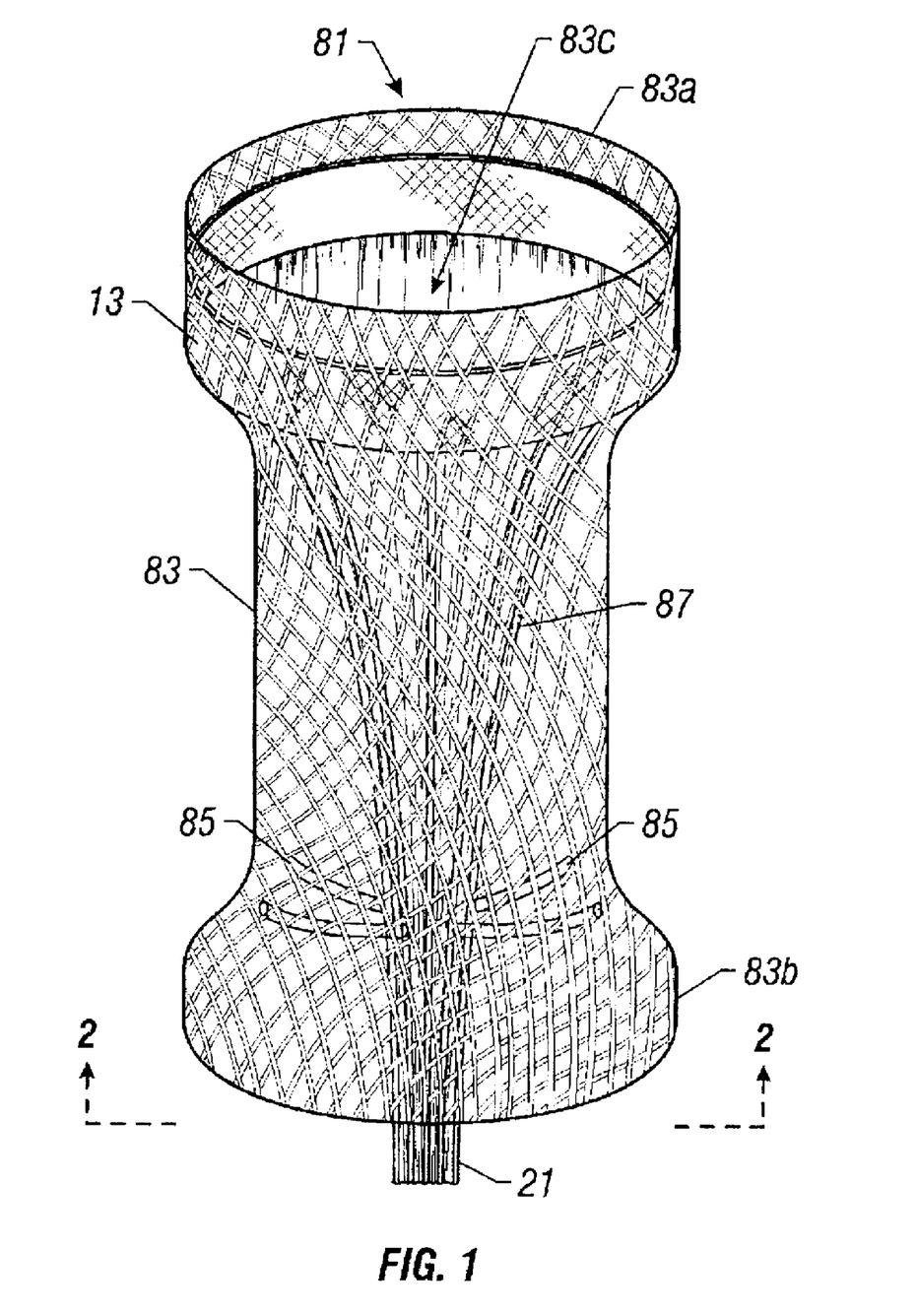
FIG. 1 is a perspective view of a preferred embodiment of the self-anchoring valve prosthesis showing a metal mesh memory material housing containing an antivalve.
Figure 11:
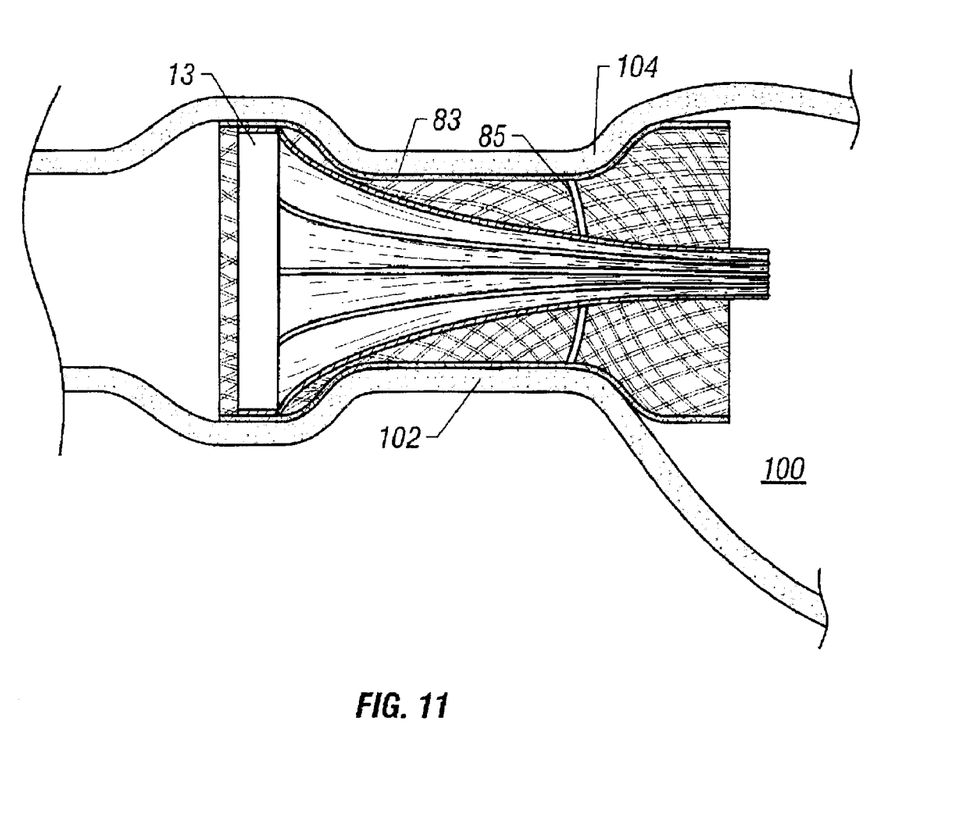
FIG. 11 is a cross-sectional view showing the valve prosthesis of FIG. 1 implanted in the gastroesophageal junction.

Referring to FIG. 1, in a preferred embodiment, the present invention provides a valve prosthesis 81 comprising a generally cylindrical housing 83 having a bell-shaped upper end 83a, a bell-shaped lower end 83b, and a central bore 83c. The upper end 83a and the lower end 83b of the cylindrical housing 83 are used by the prosthesis 81 to engage the lumen of the esophagus (see FIG. 11), and the inner diameter or central bore 83c of the cylindrical housing 83 is compatible with orthograde passage of ingested (or swallowed) material through the lumen of the esophagus.

Figure 8:
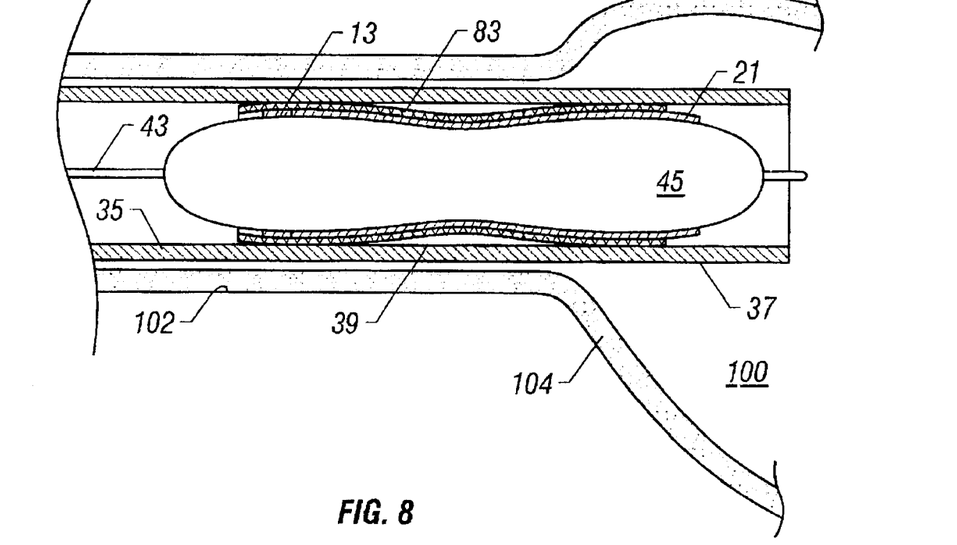
FIG. 8 is a cross-sectional view showing the valve prosthesis of FIG. 1 in an insertion tool disposed in the lumen of a patient's esophagus in an initial implantation step.
Figure 9:
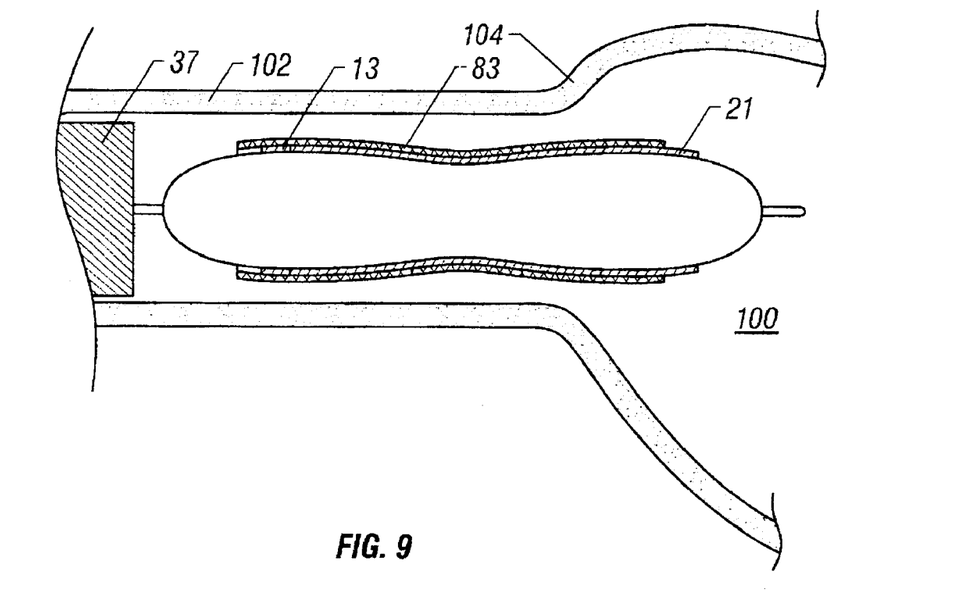
FIG. 9 is a cross-sectional view showing the valve prosthesis of FIG. 8 ejected from the distal end of the insertion tool and disposed in the lumen of a patient"s esophagus at the gastroesophageal junction in a first intermediate implantation step.
Figure 10:
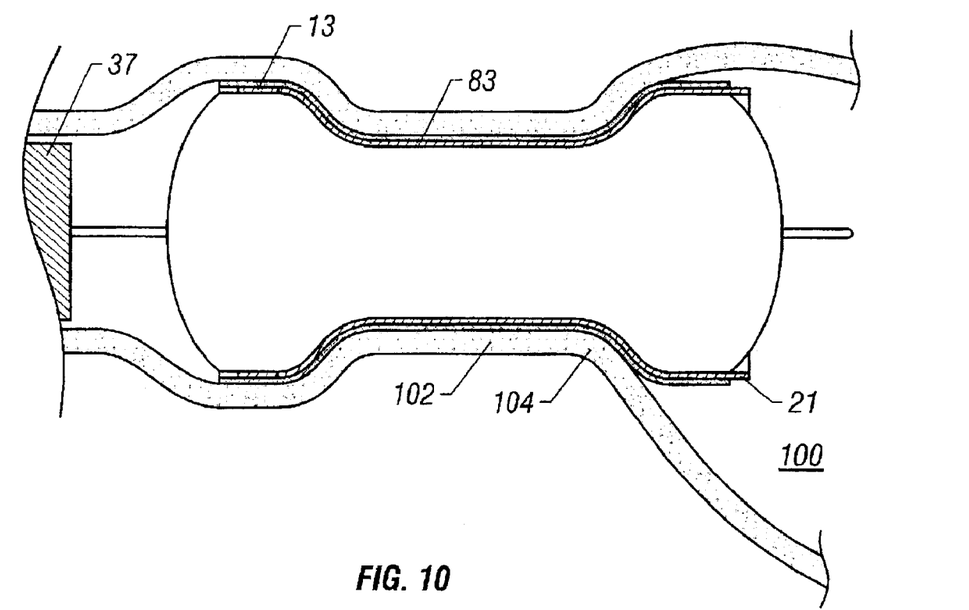
FIG. 10 is a cross-sectional view showing the valve prosthesis of FIG. 9 positioned in the gastroesophageal junction and being expanded with an inflated expansion balloon in a second intermediate implantation step.

The cylindrical housing 83 is constructed of a memory material that allows the cylindrical housing 83 to be acted upon and deformed, but to return to its original shape when the deformation force is removed. The cylindrical housing 83 is deformed during installation of the prosthesis 81 (see FIG. 8), but returns to its original shape upon release, or is expandable by a balloon, for example, to its original shape (see FIGS. 9–10). In a preferred embodiment of the present invention, the memory material comprises a metal wire mesh. The exterior surface of the metal mesh facing the esophageal wall preferably has a textured surface to promote adhesion and facilitate anchoring of the prosthesis 81 to the adjacent esophageal wall, while the interior surfaces are preferably smooth and/or hydrophobic to facilitate the orthograde passage of food and liquids therethrough. Thus, the exterior of the metal mesh can be made of or coated with microporous ceramic such as apatite, for example, hydroxyapatite, open- or closed-cell elastomer foams such as polyurethane, for example, or the like. Smooth materials for the interior surfaces of the metal mesh generally include silicone, polytetrafluoroethylene and the like.

A mounting ring 13 is fixed to the interior wall of the upper end 83a of the cylindrical housing 83. Preferably, the mounting ring 13 is constructed of the inner coating material (such as silicone) or encased or encapsulated in a suitable biologically and chemically compatible or inert material such as silicone or the like. Suspended from the mounting ring 13 within the interior of the cylindrical housing 83 is a one-way valve 21. The one-way anti-reflux valve 21 permits the easy passage of ingested material through the bore of the cylindrical housing 83 in one direction, while impeding the reflux of stomach content through the bore of the cylindrical housing 83 in the other direction.

Figure 2:
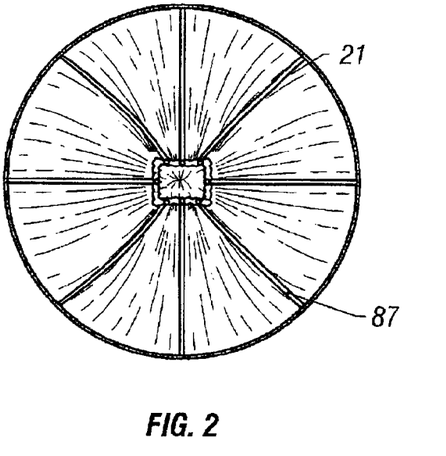
FIG. 2 is a perspective view of the one-way valve from FIG. 1 as seen from the lower end thereof along the lines 2—2.
Figure 3:
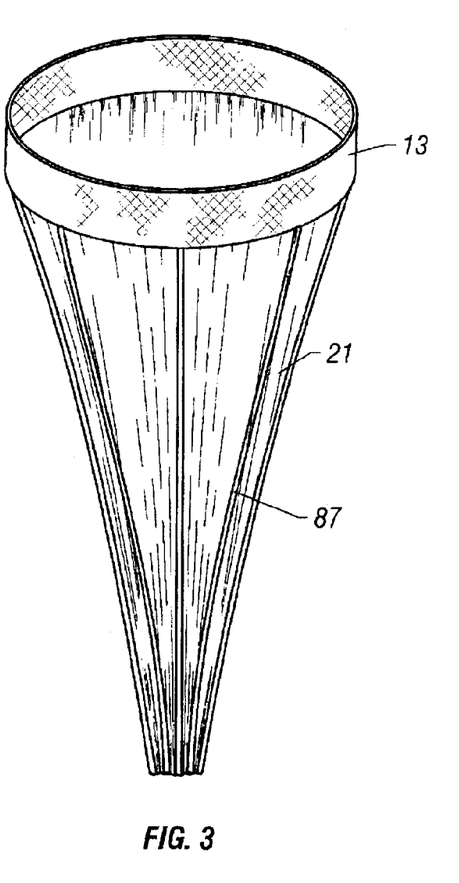
FIG. 3 is a perspective view of the valve used in the prosthesis of FIG. 2 as seen from the side.

In the embodiment seen in FIGS. 2 and 3, the valve 21 includes a sleeve 89 depending from the mounting ring 13. The sleeve 89 can be made of a biologically compatible rubber or silicone material, and preferably includes a plurality of rigid or semi-rigid longitudinal stays 87 longitudinally embedded within the material of the sleeve 89 or securely fixed on either the interior or exterior surface thereof. The stays 87 can be comprise metal wires or polymeric members, having a suitable spring-like quality to urge the sleeve 89 to close, particularly under slight gastric pressure in the stomach 100. The stays 87 can have a proximal end embedded within the mounting ring 3 to help hold the shape of the valve 21, and also serve to inhibit inversion of the sleeve 89.

The valve 21 is normally closed, and the pressure differential between the stomach 100 and the esophagus 102, and between the abdominal and thoracic cavities, act to maintain closure of the valve 21. A suitable anti-reflux valve 21 for practicing the present invention is a typical mitral or bicuspid type valve of a half-flattened cylindrical shape. Such a shape is easily suspended from the mounting ring 13 by its cylindrical end. Other valves, such as sleeve valves, monocuspid valves, hinged disk valves and double hinged valves, are practicable in the present invention by the ordinarily skilled artisan.

The bell-shaped upper end 83a and lower end 83b of the cylindrical housing 83 are used to advantage to engage the esophageal lumen 102 and the lining of the stomach 100 adjacent the gastroesophageal junction 104, respectively. Such engagement aids the mounting ring 13 in securing the prosthesis 81 within the esophagus. However, one skilled in the art will recognize that the engagement of the lumen wall 102 of the esophagus by the housing 83 in the vicinity of the mounting ring 13 alone generally provides enough resistance such that the contribution of the bell-shaped lower end 83b is merely for an additional safeguard against the prosthesis 81 being inadvertently dislocated from the esophagus.

A feature of this embodiment is the optional anti-inversion supports 85, one end of which is fixed to the lower portion of the valve 21 and the other end of which is fixed to the wall of the lower end 83b of the cylindrical housing 83. The supports 85 prevent the valve 21 from inverting. In the preferred embodiment shown in FIG. 1, the anti-inversion supports are biologically compatible ties affixed within the circumference of the interior wall of the cylindrical housing 83.

Figure 4:
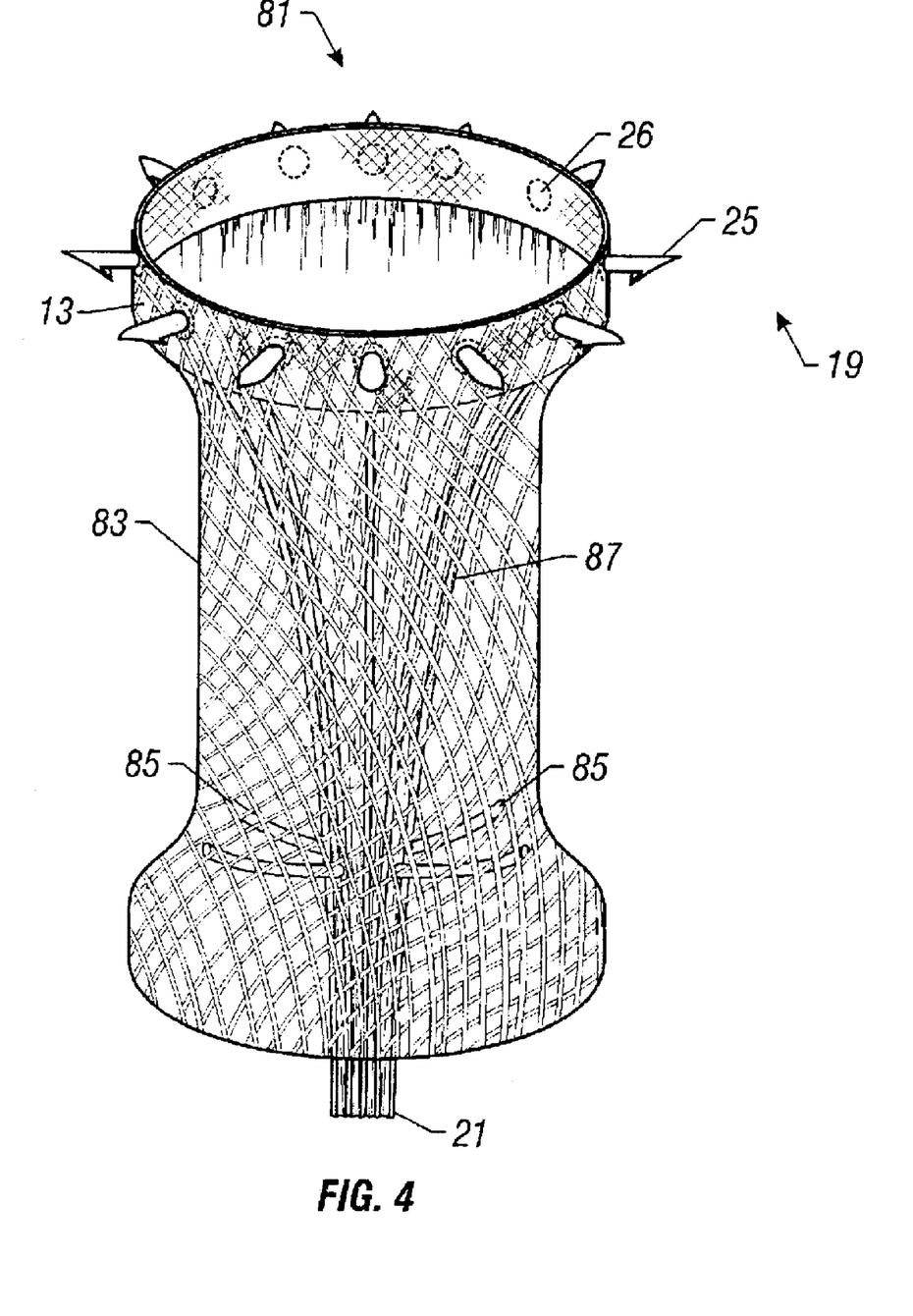
FIG. 4 is a perspective view of an alternate embodiment of the self-anchoring valve prosthesis of FIG. 1, further showing a series of barbed spikes attached to a mounting ring.

Referring to FIG. 4, the prosthesis 81 in this embodiment also includes a tissue anchor array 19 for fixing the prosthesis 81 to the lumen 100 of the esophagus. The tissue anchor array 19 extends radially outward away from the axis of the ring 13. In this embodiment, the tissue anchor array 19 is comprised of barbed spikes 25 for piercing and engaging the lumen wall of the esophagus. The tissue anchor array 19 can be comprised of at least eight spikes or points 25, but can have as many as forty or more spikes or points 25 arrayed in a plurality of rows. Each of the points 25 preferably has a laterally extending head 26 that can be fixed within the mounting ring 13, for example, by casting or curing the ring 13 with the heads 26 embedded therein so that when cured, the material of the ring 13 completely covers the heads 26. The points 25 are aligned to pass between the adjacent wires in the memory metal mesh of the upper end 83a of the housing 83, and if desired, the memory metal mesh can also be embedded in the ring 13 material prior to curing or casting so that the ring 13 is securely fixed to the housing 83.

Figure 5:
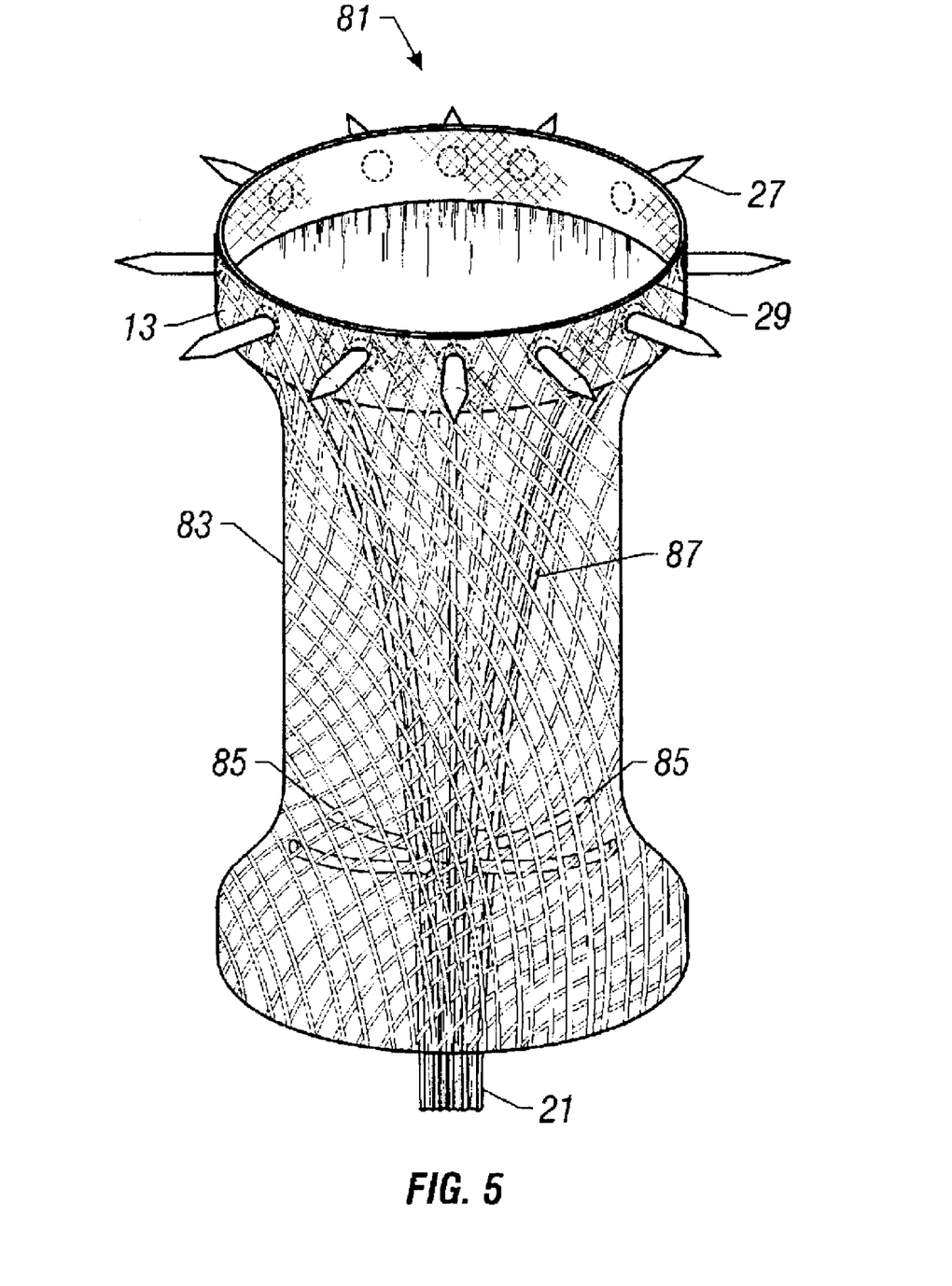
FIG. 5 is a perspective view of another alternate embodiment of the self-anchoring valve prosthesis of FIG. 1, further showing a series of uniform spikes attached to a mounting ring.

FIG. 5 illustrates another embodiment of the tissue anchor array 19. In this embodiment, the tissue anchor array 19 is comprised of straight spikes 27. The straight spikes 27 engage the lumen wall of the esophagus to secure the mounting ring 13 of the prosthesis 81, but offer the advantage of easier removal than the barbed spikes 25 of the FIG. 4 embodiment. It may be desirable or necessary at times subsequent to insertion of the prosthesis 81 to remove the prosthesis 81 from the esophagus wall. Barbed spikes 25 cause heightened resistance to removal and act to tear the esophagus wall upon removal. Thus, the uniform spikes 27 of this embodiment can be advantageously used where removal of the prosthesis 81 can be more likely.

It should be noted that in FIG. 5 the end points 29 of the wire mesh that forms the cylindrical housing 83 are affixed to the mounting ring 13 by being inserted in the mounting ring 13. However, one skilled in the art will recognize that the end points 29 can be folded over the mounting ring 13, they can be configured as shown in FIGS. 1 and 4–5, or they can be affixed to the mounting ring 13 by adhesives, etc. and remain within the purview of the invention.

Figure 6:
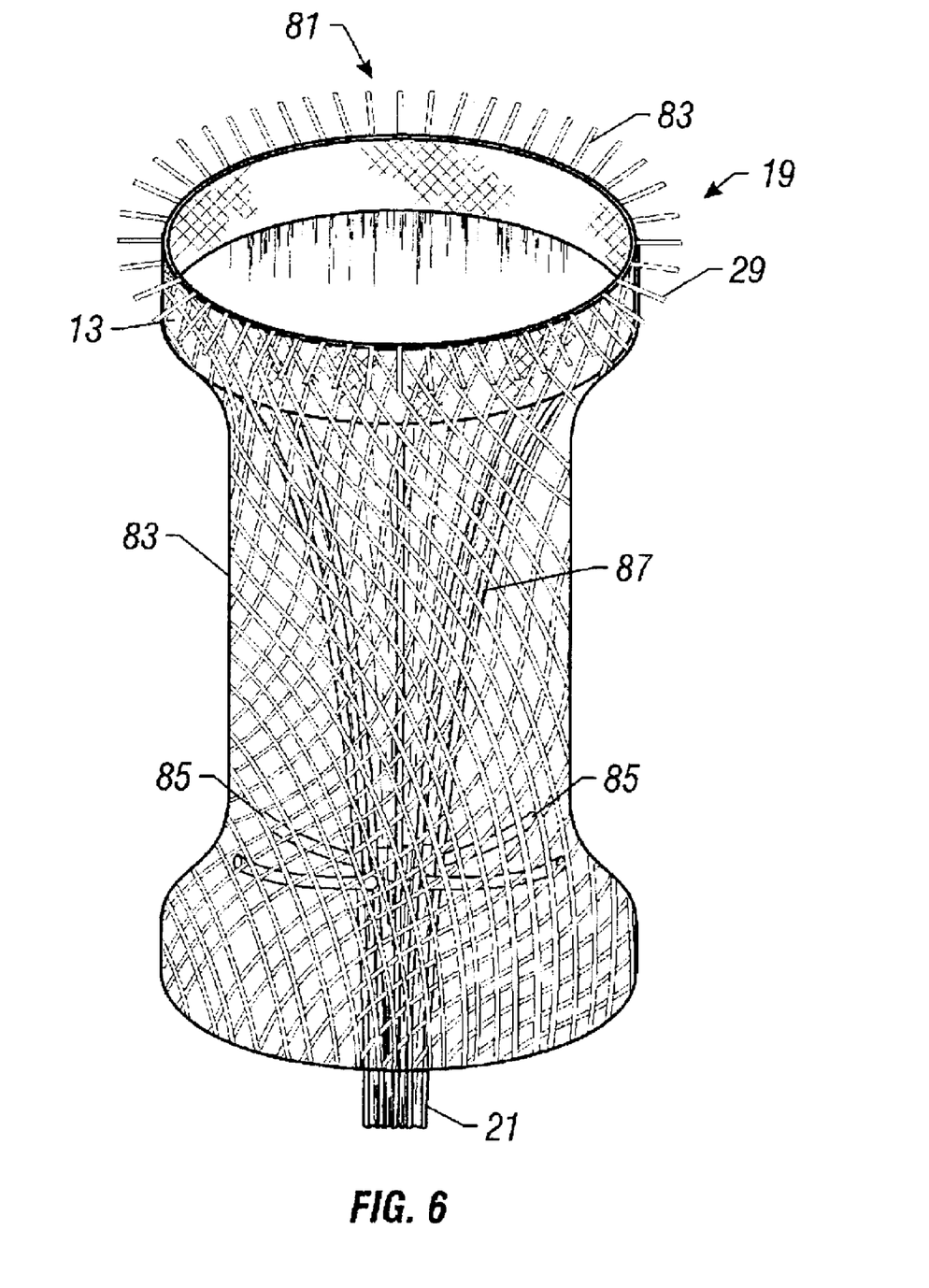
FIG. 6 is a perspective view of a further alternate embodiment of the self-anchoring valve prosthesis of FIG. 1, showing the wire mesh bent into a series of radially extending wires that function as anchoring spikes.

Yet another embodiment of the tissue anchor array 19 is illustrated in FIG. 6. In this embodiment, the tissue anchor array 19 is comprised of the end points 29 of the wire mesh that forms the cylindrical housing 83. The end points 29 of the wire mesh are bent outward such that they are pointing outwardly from the surface of the mounting ring 13. Sets of adjacent end points 29 can also be integrally wrapped together to form less flexible spikes that can penetrate the lumen wall without deformation (not shown). One skilled in the art will recognize that the end points 29 can similarly be reinforced at their tips to ensure that they can penetrate the lumen wall without deformation.

Figure 7:
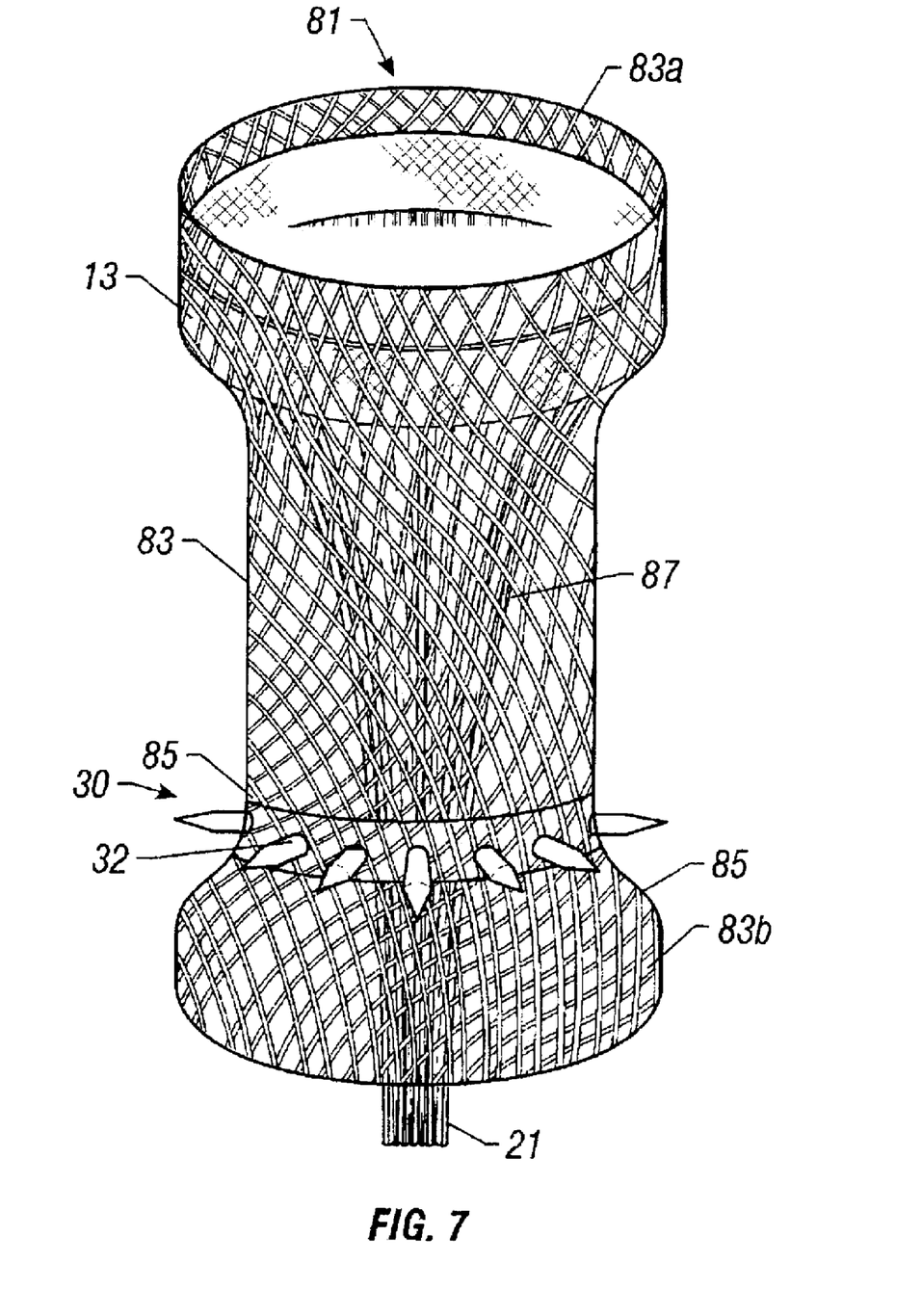
FIG. 7 is a perspective view of yet another alternate embodiment of the self-anchoring valve prosthesis of FIG. 1, further showing a series of spikes affixed to the lower end of the prosthesis.

FIG. 7 illustrates an embodiment of the valve prosthesis 81 having a tissue anchor array 30 adjacent to the bell-shaped lower end 83b of the cylindrical housing 83. In this embodiment, the tissue anchor array 30 extends radially outward from the valve prosthesis 81. The tissue anchor array 30, in combination with the inherent anchoring features of the bell shapes, provides additional safeguard that the prosthesis 81 remains secure within the esophagus. In this embodiment, the tissue anchor array 30 is comprised of points or spikes 32 for piercing and engaging the esophageal junction 104. The tissue anchor array 30 can be comprised of at least eight points or spikes 32, but can have as many as forty or more points or spikes 32 arrayed in one or a plurality of rows.

Referring to FIGS. 8–11, in one preferred embodiment, the prosthesis system of the present invention includes an implantation tool 35 for holding and perorally inserting a prosthesis 81 down the lumen of a patient's esophagus to a position proximate the gastroesophageal junction, and fixing the prosthesis 81 to the lumen wall. The tool 35 comprises a flexible overtube 37, of a construction and length suitable for peroral insertion into the esophagus. At one end, the overtube 37 has an integral compression collar 39 and at the other end a conventional handle (not shown) for manipulation. The compression collar 39 provides a means for releasably receiving the housing 83 of the prosthesis 81 in a compressed configuration. A hollow stylet 43 is slidably contained (or indwelling) in the length of the overtube 37 from end to end. At the collar 39 of the overtube 37, the stylet 43 has a balloon 45 attached. The bladder of the balloon 45 communicates with the hollow (not shown) of the stylet 43, and the balloon 45 is inflatable by pressurizing the hollow of the stylet 43 with a gas or liquid inserted into the hollow from the handle end of the tool 35.

It should be noted that because the cylindrical housing 83 of the prosthesis 81 is comprised of a memory material, depending upon the application environment, the balloon 45 within the overtube 37 may not be necessary for secure engagement of the mounting ring 31 to the esophagus. The prosthesis 81 can be secured within the esophagus by placing the compressed prosthesis 81 within the overtube 37, positioning the overtube 37 within the esophagus, and releasing the prosthesis 81 from the overtube 37 in or near the gastroesophageal junction 104 . Once released, the cylindrical housing 83 springs back or is expanded by inflation of the balloon 45 to its initial form, thereby engaging the lumen wall 102 of the esophagus. The balloon 45 is then deflated for removal of the tool 35.

While the above description contains many specifics, these should not be construed as limitations on the scope of the invention, but rather as exemplifications of preferred embodiments thereof. Many other variations are possible, which would be obvious to one skilled in the art. Accordingly, the scope of the invention should be determined by the scope of the appended claims and their equivalents, and not just by the illustrative embodiments.

What is claimed is:

1. A sutureless, perorally insertable anti-reflux valve prosthesis, comprising:
   a cylindrical housing constructed of a memory material comprising a metal mesh;
   a mounting ring fixed to the housing;
   a one-way sleeve valve depending from the mounting ring within the cylindrical housing; and
   a plurality of longitudinally aligned stays operatively associated with the sleeve and disposed within the cylindrical housing for inhibiting inversion of the sleeve.

2. The anti-reflux valve prosthesis of claim 1 wherein the metal mesh further comprises an interior surface and an exterior surface, the exterior surface being textured to facilitate anchoring of the prosthesis, and the interior surface being smooth to facilitate orthograde passage of foods and liquids therethrough.

3. The anti-reflux valve prosthesis of claim 1 wherein the memory material is selected from the group consisting of nickel, titanium alloy, spring steel, and plastic.

4. The anti-reflux valve prosthesis of claim 1 wherein the memory material is encased in silicone.

5. The anti-reflux valve prosthesis of claim 1 wherein the cylindrical housing has an enlarged upper end.

6. The anti-reflux valve prosthesis of claim 5 wherein the cylindrical housing further comprises an enlarged lower end.

7. The anti-reflux valve prosthesis of claim 1 further comprising an array of tissue anchors having spikes for piercing and engaging the lumen wall of an esophagus and fixing the mounting ring in the lumen of the esophagus.

8. The anti-reflux valve prosthesis of claim 1 further comprising an anti-inversion support having two ends, one end of which is fixed to the one-way valve and the other end of which is fixed to the wall of the lower end of the cylindrical housing to prevent the valve from inverting.

9. The anti-reflux valve prosthesis of claim 1, further comprising:
   an overtube for holding the cylindrical housing in a radially compressed condition at a distal end of the overtube for peroral insertion down an esophageal lumen;
   a stylet indwelling in the overtube in releasable operative engagement with the housing to eject the housing from the distal end of the overtube.

10. The anti-reflux valve prosthesis of claim 9 further comprising a balloon at a distal end of the stylet in the cylindrical housing, wherein the balloon is in fluid communication with a central longitudinal passage in the stylet for introducing fluid into the balloon to facilitate expansion of the housing to its normal cross-section following ejection of the housing from the overtube, and for removing said fluid from the balloon to allow retraction of the balloon from the housing into the overtube.

11. An anti-reflux valve prosthesis comprising:
    a cylindrical housing having an enlarged upper end, a lower end, and an interior defined by an interior wall, the cylindrical housing constructed of a memory material having a normal cross-section, such that when a force, applied to the housing to make the cross-section smaller, is removed, the housing returns to its normal cross-section or is expandable to its normal cross-section;
    a mounting ring fixed to the wall of the upper end of the housing;
    a one-way valve depending from the mounting ring within the interior of the cylindrical housing comprising a sleeve and a plurality of longitudinal stays associated therewith; and
    an optional anti-inversion support having two ends, one end of which is fixed to a lower end of the one-way valve and the other end of which is fixed to the wall of the lower end of the cylindrical housing.

12. The anti-reflux valve prosthesis of claim 11 wherein the memory material is a metal mesh.

13. The anti-reflux valve prosthesis of claim 11 wherein the metal mesh further comprises an interior surface and an exterior surface, the exterior surface being textured to facilitate anchoring of the prosthesis, and the interior surface being smooth to facilitate orthograde passage of foods and liquids therethrough.

14. The anti-reflux valve prosthesis of claim 11 wherein the memory material is selected from the group consisting of nickel, titanium alloy, spring steel, and plastic.

15. The anti-reflux valve prosthesis of claim 11 wherein the memory material is encased in silicone.

16. The anti-reflux valve prosthesis of claim 11 wherein the housing further comprises a tissue anchor array.

17. The anti-reflux valve prosthesis of claim 11 comprising a plurality of the anti-inversion supports.

18. The invention of claim 11 wherein the lower end of the cylindrical housing comprises a bell shaped lower end.

19. The invention of claim 18 further comprising a tissue anchor array adjacent the lower end of the cylindrical housing.

20. A method for implanting an anti-reflux valve prosthesis adjacent the esophageal Junction, comprising:
    perorally inserting an anti-reflux valve prosthesis in a radially compressed condition down a non-cancerous esophageal lumen, wherein the anti-reflux valve prosthesis comprises a cylindrical housing constructed of a memory material, a mounting ring fixed to the housing and a one-way valve depending from the mounting ring within the cylindrical housing;
    positioning the compressed anti-reflux valve prosthesis near the esophageal junction; expanding the anti-reflux valve prosthesis to normal cross-section to implant said prosthesis in the esophageal junction.

21. The method of claim 20 wherein the insertion is effected with the valve prosthesis in an overtube, the positioning includes ejecting the valve prosthesis from the overtube, and the expanding optionally comprises inflating a balloon inside the valve prosthesis.

22. The method of claim 20 wherein the prosthesis includes an array of tissue anchors and the method further comprises inserting the tissue anchors in the lumen of the esophagus to fix the prosthesis in place.

23. The method of claim 22 wherein the mounting ring is disposed at an upper end of the cylindrical housing and the one-way valve is a sleeve valve having longitudinal stays to prevent inversion of the valve.

24. The method of claim 20 wherein the mounting ring is disposed at an upper end of the cylindrical housing.

25. A sutureless, perorally insertable anti-reflux valve prosthesis, comprising:

a cylindrical housing constructed of a memory material;

a mounting ring fixed to the housing;

a one-way valve depending from the mounting ring within the cylindrical housing; and an anti-inversion support having two ends, one end of which is fixed to the one-way valve and the other end of which is fixed to a wall of a lower end of the cylindrical housing to prevent the valve from inverting.

\* \* \* \* \*